United States Patent
Rhodes

(10) Patent No.: US 6,453,204 B1
(45) Date of Patent: Sep. 17, 2002

(54) MAGNETIC ELECTRODE FOR DELIVERING ENERGY TO THE BODY

(76) Inventor: Donald A. Rhodes, 4833 S. Staples, Corpus Christi, TX (US) 78411

( * ) Notice: Subject to any disclaimer, the term of this patent is extended or adjusted under 35 U.S.C. 154(b) by 15 days.

(21) Appl. No.: 09/637,055

(22) Filed: Aug. 11, 2000

(51) Int. Cl.⁷ .................................................. A61N 1/00
(52) U.S. Cl. ........................................ 607/149; 600/15
(58) Field of Search ........................ 600/9–15; 607/149

(56) References Cited

U.S. PATENT DOCUMENTS

| | | |
|---|---|---|
| 4,233,965 A | 11/1980 | Fairbanks |
| 4,550,714 A | 11/1985 | Talish |
| 4,556,051 A | 12/1985 | Maurer |
| 4,765,310 A | 8/1988 | Deagle |
| 4,940,453 A | 7/1990 | Cadwell |
| 5,092,835 A | 3/1992 | Schurig |
| 5,147,284 A | * 9/1992 | Fedorov et al. |
| 5,478,303 A | 12/1995 | Foley-Nolan |
| 5,700,234 A | 12/1997 | Masuda |
| 5,772,688 A | * 6/1998 | Muroki |
| 5,995,873 A | * 11/1999 | Rhodes |

* cited by examiner

Primary Examiner—Mark Bockelman
(74) Attorney, Agent, or Firm—G. Turner Moller

(57) ABSTRACT

A magnetic electrode is used to deliver electrical energy into the body of a patient to promote healing. The electrode includes a conductive path having a lead for connection to a device for delivering electrical energy to the patient. The electrode also includes one or more disc shaped permanent magnets having one side of all north polarity and another side of all south polarity. The magnetic field generated by the magnet assembly includes force lines generally perpendicular to the patient's body. In one embodiment, the magnet is attached to the electrode. In a second embodiment, the magnet is carried by a sock. In a third embodiment, the magnet is carried by a glove.

21 Claims, 2 Drawing Sheets

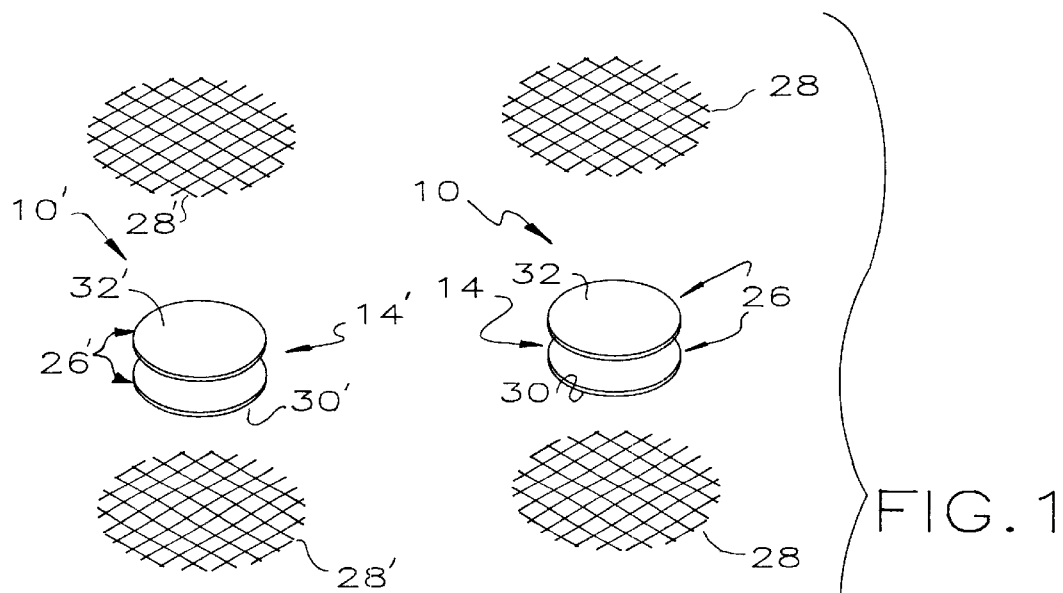
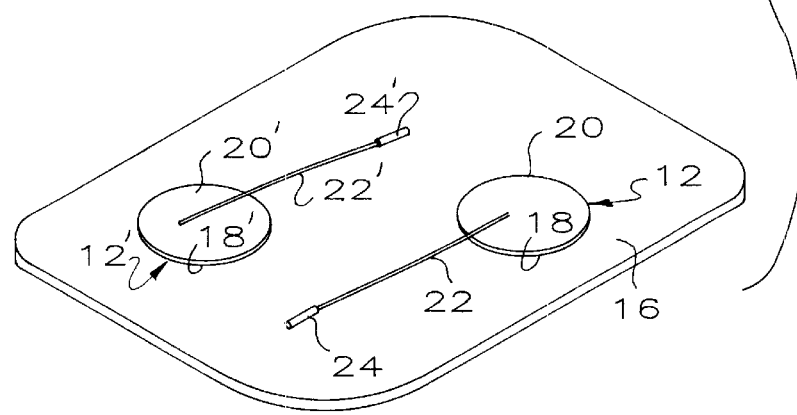
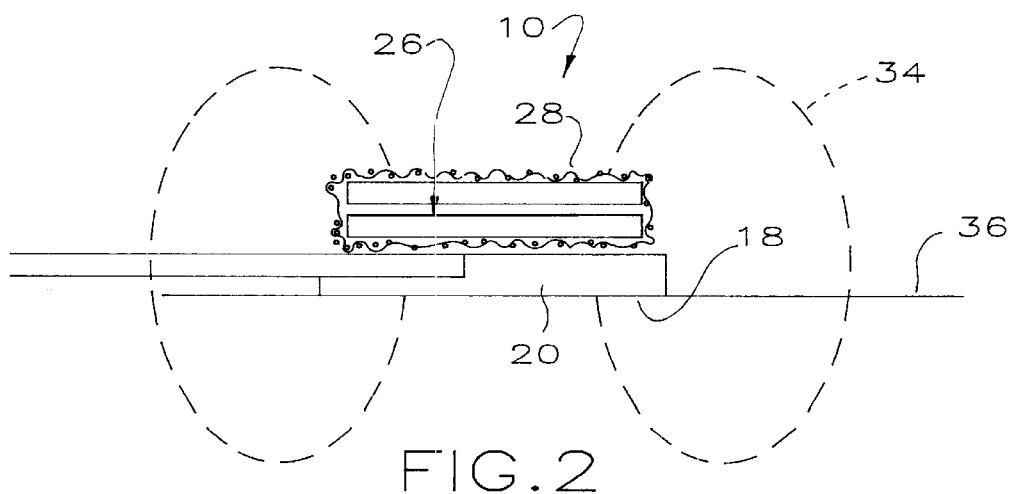
FIG. 1
FIG. 2

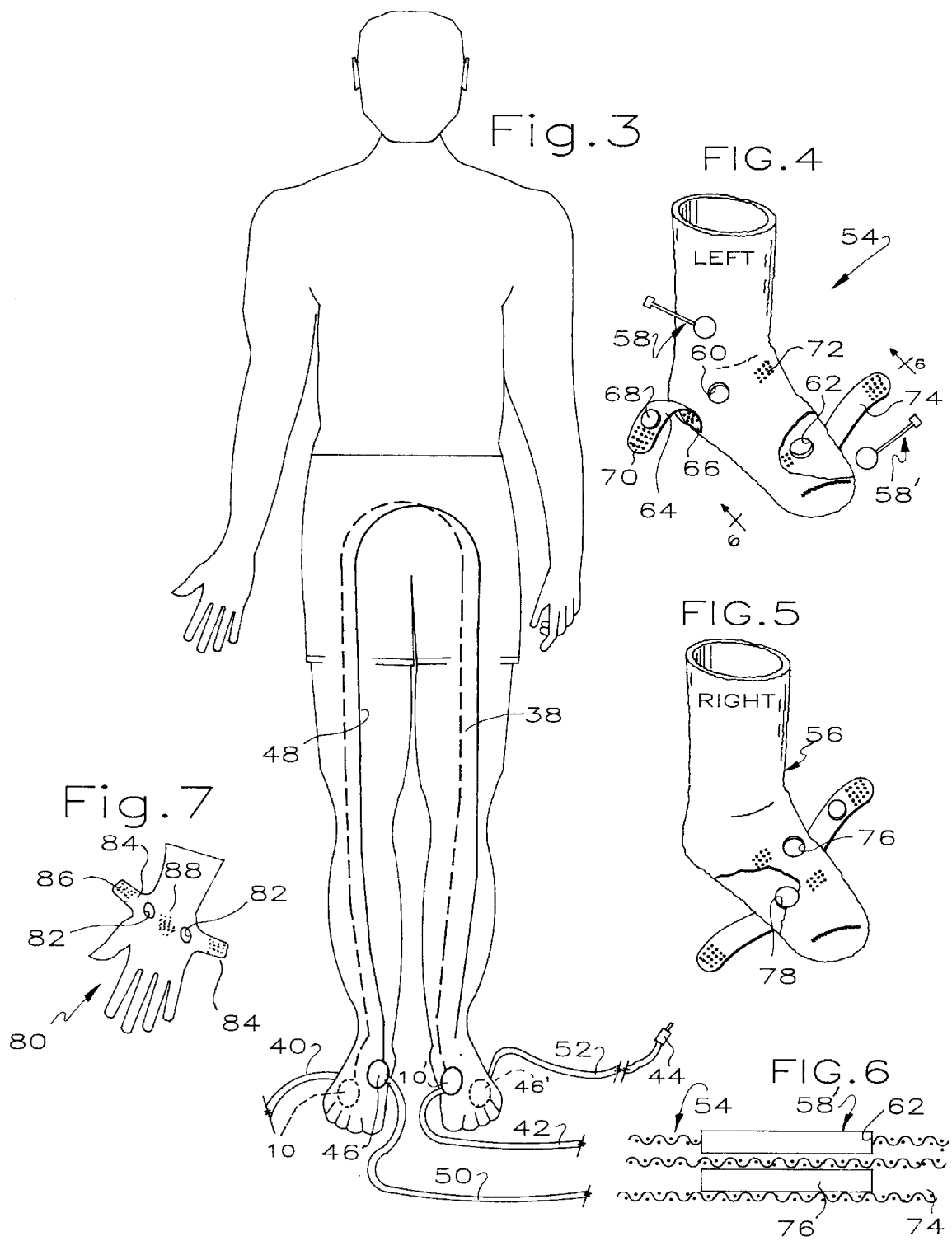

MAGNETIC ELECTRODE FOR DELIVERING ENERGY TO THE BODY

This invention comprises an electrode for use in delivering electrical energy into the body for the purpose of creating changes in the somatic and autonomic nervous system.

BACKGROUND OF THE INVENTION

It is well known in the art to treat pain or other symptoms by the application of energy in the form of alternating current electricity, magnetism and other forms of electromagnetic energy. As disclosed in U.S. Pat. No. 5,995,873, the disclosure of which is incorporated herein by reference, a patient is treated by establishing a circuit in the patient's body to include at least part of the spinal column. In one technique, this is done with electrical interferential therapy using conventional electrodes making connection between the energy source and the patient's body.

It is also known to treat patients on the basis of improving the sodium-potassium pump operating at a cellular level. Human cells contain a bioelectrical potential across the cell membrane. This is generated by the concentration of sodium and potassium ions inside and outside the cell. Under equilibrium conditions, the electrical currents caused by the movement of sodium and potassium ions through the semipermeable membrane are equal, resulting in a zero net current and a resting potential of approximately zero. The sodium pump is an active transport system which selectively removes sodium from the interior of the nerve to the exterior and returns potassium to the interior from the exterior. This results in a resting potential of about −90 millivolts. When the cell is electrically stimulated by a nerve signal or by an external stimulus, the cell passes through a cycle. The sodium ionic current into the cell increases until the cell's internal voltage reaches a threshold of about −60 millivolts, when the cell potential increases without further stimulation to a peak of about +20 millivolts. The cell then repolarizes to about −90 millivolts, due to the action of the sodium pump. This cell activity has been referred to as the sodium-potassium pump, as generally described in Biophysical Measurements, p 7–21, by Peter Strong (1971).

The sodium-potassium pump is important in the maintenance of health and is normally provided by ordinary nerve signals in healthy specimens. When ordinary nerve signals are interrupted, as by trauma or arthritis, the sodium-potassium pump is disrupted. Application of external voltage pulses is thought to assist in reestablishing cell action within the affected area and thereby promote healing.

One well accepted technique for treating small areas for pain or other symptoms is known as electrical interferential therapy in which electrodes are connected in a crossing pattern adjacent the area to be treated. Alternating current is delivered through the electrodes into the body. Such devices are commercially available from Dynatronic Corporation of Salt Lake City, Utah or Rehabilicare Corporation of St. Paul, Minn. This type equipment is used to treat small areas of the body because the electrodes are spaced relatively close together in the region to be treated.

Magnetic electrodes are known in the prior art for delivering electrical energy into the body for therapeutic purposes as shown in U.S. Pat. Nos. 4,223,965; 4,550,714; 4,556,051; 4,765,610; 4,940,453; 5,092,835; 5,478,303; and 5,700,234.

SUMMARY OF THE INVENTION

In this invention, an electrode assembly comprises a permanent magnet and means for delivering electrical energy into the body. The magnet is designed so that the magnetic field is generally perpendicular to the body providing an aid to penetration of the applied electric current into the deep tissues. Because the magnet is a permanent magnet, the magnetic field acts continuously to assist the electric current to penetrate the tissue adjacent the electrode. The permanent magnet has a strength of at least about 100 gauss and preferably is at least about 2400 gauss.

Without being bound by any theory of operation, the premise of this invention is that magnetic lines of force may be created that add to the electromotive force of electrical energy being delivered into a patient's body. When these forces add, electrical energy is more efficiently delivered into the body.

Use of the device is preferably as shown in U.S. Pat. No. 5,995,873 where a circuit is set up in the patient's body. This device may also be used in a more conventional manner to treat localized pain or symptoms.

It is an object of this invention to provide an improved electrode for delivering electrical energy into the body.

Another object of this invention is to provide an improved magnetic electrode.

These and other objects and advantages of this description will become more apparent as this description proceeds, reference being made to the accompanying drawings and appended claims.

BRIEF DESCRIPTION OF THE DRAWINGS

FIG. 1 is an exploded isometric view of a magnetic electrode of this invention;

FIG. 2 is a pictorial cross-sectional view showing the lines of magnetic force in the electrode of FIG. 1;

FIG. 3 is a pictorial view of the use of this invention;

FIG. 4 is an isometric view of a sock used in this invention;

FIG. 5 is an isometric view of another sock used in this invention;

FIG. 6 is a cross-sectional view of FIG. 4, along line 6—6 thereof, as viewed in the direction indicated by the arrows; and FIG. 7 is an isometric view of a glove used in this invention.

DETAILED DESCRIPTION

Referring to FIGS. 1–2, a magnetic electrode 10 of this invention comprises, as major components, an electrically conductive patch 12 and a permanent magnet assembly 14. A mate 10' to the electrode 10 comprises an electrically conductive patch 12' and a permanent magnet assembly 14'. A pair of the magnetic electrodes 10, 10' are shipped on a substrate 16.

The electrically conductive patches 12, 12' include an adhesive layer 18, 18' bonded to the substrate 16, a conductive layer or patch 20, 20' and an electrical wire or lead 22, 22' having a fitting 24, 24' for connection to an interferential machine (not shown) as more fully apparent hereinafter. The electrically conductive patches 12, 12' are commercially available from Dynatronic Corporation of Salt Lake City, Utah.

The permanent magnet assembly 14, 14' includes a pair of permanent magnets 26, 26' housed in a fabric cover 28, 28' secured to the conductive layer 20, 20' in any suitable manner, as by an adhesive layer, a captivating enclosure, a hook-and-loop fastener such as VELCRO, or the like. The permanent magnets 26, 26' are commercially available from Magnetic Therapeutic Technologies, Inc. of Irving, Tex. as a Model MTT Flexible Magnet. The magnets 26, 26' are made of a composite material having a resin base impregnated with a magnetic powder. Preferably the magnets are slightly resilient, so they can be taped to the body of a patient and conform to the configuration of the locale where they are attached. The magnets 26, 26' together provide a magnetic field having a strength of at least 100 gauss and preferably a strength of at least 2400 gauss.

The magnets 26, 26' are of disc shape having one side 30, 30' that is of all north pole polarity and another side 32, 32' that is all of south pole polarity. This creates a magnetic field as suggested in FIG. 2 where the magnetic force lines 34 extend perpendicular to the patch 12 and thus perpendicular to the body 36 of the patient. The direction of the force of the magnetic field depends on whether the magnet 30 having the north pole down is adjacent the patient's skin or whether the magnet 30' having the south pole down is adjacent the patient's skin. Because the magnets 26 are circular, the magnetic field is in the shape of a torus.

The magnetic electrodes of this invention are almost always used in pairs to create a circuit through the patient's body as will be explained more fully hereinafter. The magnets of the electrode 10 has the north pole down so it is placed adjacent the skin of the patient. The magnets of the electrode 10' have the south pole down so the electrode 10, is placed adjacent the skin of the patient. In a situation where the patient has greater pain or greater involvement on one extremity than the other, the electrode 10 having the magnets with the north pole down is preferably placed on the extremity with the greater pain or involvement because the results seem to be better. In other situations, the electrode 10 having the north pole down is preferably placed on the left extremity.

The electrodes 10, 10' of this invention are preferably used in the method shown in U.S. Pat. No. 5,995,873 and as shown in FIG. 3. The electrodes 10, 10' are thus preferably used in pairs to complete a circuit in the human body. The electrodes 10, 10' are attached to the patient's skin in a conventional manner, i.e. they are self adherent because of the adhesive layers 18, 18'. The location of the electrodes 10, 10' on the patient establish the electrical circuit in the patient's s body. The permanent magnets may be juxtaposed over the electrically conductive patches in a variety of manners. The electrically conductive patches can be affixed to the magnet with an adhesive, held in position relative to the magnet by hook-and-loop fasteners, elastic bands with hood-and-loop attachments, or tape. Any of these can be used in conjunction with a marker sock or glove.

One example is shown in FIG. 3 where the electrode 10 is placed adjacent the end or terminus of the right lateral plantar nerve L5 and its matching electrode or mate 10' is placed adjacent the end or terminus of the left saphenous nerve L4, inferior to the left ankle bone (medial malleolus) thereby establishing or creating a first circuit 38 in the patient's s body. As used herein, the reference characters L4, L5, and the like are standard medical terminology for the nerve. Those skilled in the art will recognize L4 as being the nerve which extends away from the fourth lumbar vertebra and L5 as being the nerve which extends away from the fifth lumbar vertebra. Those skilled in the art will recognize that the terminus of the right lateral plantar nerve L5 is located on the bottom of the right foot. The terminus of the left saphenous nerve L4 is located in front of the left ankle bone (medial malleolus).

The fittings (not shown) of the electrodes 10, 10' are connected to wires 40, 42 leading to a connector 44 which connects to the interferential machine (not shown) such as is available from Dynatronic Corporation of Salt Lake City, Utah or other source of electrical energy.

Preferably, the magnetic electrodes of this invention are used in at least two pairs. Thus, another electrode 46 is placed adjacent the terminus of the right saphenous nerve L4 and its matching electrode or mate 46' is placed adjacent the terminus of the left lateral plantar nerve L5 thereby establishing a second circuit 48 in the patient's s body. The fittings (not shown) of the electrodes 46, 46' are connected to wires 50, 52 connected to the interferential machine (not shown) or other source of electrical energy. Ideally, the magnetic electrodes of this invention are used in at least four pairs as shown in U.S. Pat. Nos. 5,995,873 to which reference is made for a description of a four pair system.

Turning the interferential device (not shown) on delivers electrical energy through the circuits 38, 48. Experience has shown a decrease in pain in patients complaining of pain and a decrease in symptoms consistent with an imbalanced sympathetic nervous system. Those skilled in the art will recognize that the lateral plantar nerves L5 and the saphenous nerves L4 terminate adjacent the spinal column near adjacent spinal vertebra, in the area of the connection to the lumbar sympathetic ganglia.

As shown in FIGS. 4 and 5, one or more socks 54, 56 may be provided to position electrically conductive patches 58, 58' correctly relative to the nerves to which electrical connection is made. In this regard, the patches 58, 58' are conveniently identical to the patches 12, 12'. To this end, the sock 54 provides openings 60, 62 for receiving the patches 58, 58'. The openings 60, 62 correspond to the location of the left saphenous nerve L4 and the left lateral plantar nerve L5 respectively.

A flap or band 64 is stitched to the sock 54 along one end 66 adjacent the opening 60 and carries one or more magnets 68. The band 64 may be of an elastic or inelastic material. Any suitable fastening means, such as hook-and-loop fasteners halves 70, 72, are provided on the flap 64 and the sock 54. In this manner, the flap 64 is movable from an inoperative position shown in FIG. 4 so the conductive patch 58 may be inserted through the opening 60 and an operative position where the magnets 68 overlie the conductive patch 58. A similar flap or band 74 is provided with magnets 76 sewn inside it to overlie the opening 62, as shown in FIG. 6.

The concept behind the socks 54, 56 is to provide a tool or adjunct so a lay person can position the patches 58, 58' correctly. This is accomplished by in a simple and foolproof manner of positioning the conductive patches 58, 58' in their appropriate position on the patient and securing the magnets 68 relative to the patches 58.

It will be seen that the sock 54 is a left sock that positions the electrodes 58, 58' in the position shown in FIG. 3. A right sock 56 is also needed to position the conductive patches 74, 74' in the position shown on the right foot in FIG. 3. To this end, the sock 56 provides openings 76, 78 for receiving the conductive patches 74, 74'. The openings 76, 78 correspond to the location of the right saphenous nerve L5 and the right lateral plantar nerve L4 respectively. The conductive patches 74, 74' are substantially identical to the conductive patches 12, 12'. In the alternative, the electrodes 58, 58' may be sewn into the sock 54 in a position corresponding to one of the nerve positions with the electrodes exposed for connection to the interferential device.

Referring to FIG. 7, a glove 80 is an example of another fitted extremity covering used in this invention. The glove 80 provides at least a pair of openings 82 for receiving one of the magnetic electrodes of this invention. A flap 84 is provided for covering the opening 82 and thereby captivating the electrode. A suitable fastening system, such as hook-and-loop devices 86, 88 allow the flap 84 to be manipulated to uncover and cover the openings 82. In the alternative, the electrodes may be sewn into the gloves at suitable locations or the magnets can be sewn into the gloves or socks so that the sock or glove can be slid over the top of the previously applied conductive patch 20.

It will be apparent that a variety of socks and gloves will be provided, having openings superposed over the nerve endings in the foot or hand of a patient adjacent the termini of nerves. The position of the openings will vary, depending on which nerves comprise the circuits in the body.

Use of the electrode of this invention is shown in the following examples:

EXAMPLE 1

A 30 year old Caucasian woman, with Reflex Sympathetic Dystrophy Syndrome, was treated on 15 consecutive days with interferential therapy in accordance with this invention. Two pairs of circuits were created. The first half of the first circuit pair was from the right foot saphenous nerve to the left foot lateral plantar nerve. The second half of the first circuit pair was from the right foot lateral plantar nerve to the left foot saphenous nerve. The first half of the second circuit was from the left foot medial plantar nerve to the right foot sural nerve. The second half of the second circuit pair was from the right foot sural nerve to the left foot medial plantar nerve. 4800 gauss magnets were placed over the first circuit pair of electrodes on each foot, with the North pole of the magnet closer to the left foot and the South Pole of the magnets closer to the right foot. Electrical energy was delivered through an interferential machine made by Dynatronic Corporation of Salt Lake City, Utah for thirty minutes during each treatment for a series of thirty treatments. At the end of these treatments, the patient was markedly improved. A marker sock was used to align the electrodes with the underlying nerves. An elastic band with magnets sewn to it was used to align the magnet in close approximation to the underlying electrically conductive patch.

EXAMPLE 2

A 64 yard old Caucasian woman was seen with a focal peripheral neuropathy, in the right 3rd interspace (Morton's neuroma). This was treated utilizing a Spectrum (TENS) unit made by Rehabilicare Corporation of St. Paul, Minn. The first magnet was placed over the electrically conductive patch on the plantar aspect of the right 3rd interspace, with the North pole closer to the skin. The second magnet was placed over the electrically conductive patch on the dorsal aspect of the right 3rd interspace, with the South pole closer to the skin. Each of the magnets had an appropriate hook-and-loop fastener to allow easy attachment to the corresponding fastener on the electrically conductive patch. 4800 gauss magnetic electrodes of this invention were utilized. Electrical energy was delivered for forty minutes during a treatment for a series of fifteen treatments. At the end of these treatments, the patient was markedly improved.

EXAMPLE 3

A 52 year old Caucasian male was seen with a very sore "tennis elbow", in the right arm. This was treated utilizing a Dynatron 650 RS unit, in which channels 1 and 2 became the first interferential treatment while channels 3 and 4 became the second interferential treatment. These treatments were given simultaneously. The first interferential therapy was given from the right thumb, palmar surface (C6) to the left 5th finger, palmar surface (C8); and from the right 5th finger, palmar surface (C8) to the left thumb, palmar surface (C6). At the same time, a second interferential therapy was given, through the right elbow, forming a "cross". The first pair of leads was placed on the medial and lateral aspect of the right elbow, forming the first leg of the "cross". The second pair of leads was placed on the proximal and distal aspect of the right elbow, forming the second leg of the cross. A 4800 gauss magnet was placed with the North pole down (closer to the skin) and was positioned over the electrically conductive patch on the lateral aspect of the elbow. A 4800 gauss magnet was placed with the South pole down (closer to the skin) over the electrically conductive patch on the medial aspect of the elbow. Each of the magnets had an appropriate hook-and-loop fastener to allow easy attachment to the corresponding fastener on the electrically conductive patch. The second pair of leads (forming the second leg of the cross) utilized standard non-magnetic electrodes. At the end of the first treatment, the patient was markedly improved.

EXAMPLE 4

An 11 year old boy developed a pathological fracture, through an area of subchondral cystic degeneration, in the base of the right 1st metatarsal. He was treated daily, for 4 weeks, with doubled interferential therapy using magnetic electrodes. The first interferential therapy was given from the plantar aspect of the right 2nd metatarsal head (medial plantar nerve—L5) to the anterior-medial aspect of the left ankle (saphenous nerve—L4). The other half of the first interferential therapy was given from the anterior-medial aspect of the right ankle (saphenous nerve—L4) to the plantar aspect of the left 2nd metatarsal head (medial plantar nerve—L5). At the same time, a second interferential therapy was given in the form of a "cross", through the area of the fracture. The 1st pair of leads of the second interferential therapy was placed on the medial and lateral aspect of the right foot, to form a line through the area of fracture. The 2nd pair of leads of the second interferential therapy was placed on the dorsal and plantar surface of the right foot to form a line through the area of fracture. A 4800 gauss magnet was placed with the North pole directed toward the skin over the electrically conductive patch of the plantar aspect of the right foot, beneath the area of fracture. Another 4800 gauss magnet was placed with the South pole directed toward the skin over the electrically conductive patch on the dorsal aspect of the right foot, over the area of fracture. Each of the magnets had an appropriate hook-and-loop fastener to allow easy attachment to the corresponding fastener on the electrically conductive patch. X-rays obtained following the four weeks of treatment showed resolution of the subchondral cystic degeneration and the pathological fracture.

EXAMPLE 5

A 30 year old African-American female presented with a 1 cm diameter necrotic ulceration, lateral aspect of the right ankle; complicated by the presence of Sickle Cell Anemia. This ulceration had been treated unsuccessfully, with multiple treatments. She was treated daily, for five weeks, with doubled interferential therapy using magnetic electrodes. The first half of the first interferential therapy was given from the dorsal aspect of the right 2nd interspace (intermediate dorsal cutaneous nerve—L5) to the lateral aspect of the left hallux (deep peroneal nerve—L4). The other half of the first interferential therapy was given from the lateral aspect of the right hallux (deep peroneal nerve—L4) to the dorsal aspect of the left 2nd interspace (intermediate dorsal cutaneous nerve—L5). The first pair of leads of the second interferential therapy was placed slightly anterior and posterior to the ulceration, approximately one centimeter from the ulceration. The second pair of leads of the second interferential therapy was placed slightly anterior and posterior to the ulceration, approximately one centimeter from the ulceration. A 4800 gauss magnet was placed with the North pole directed toward the skin over the electrically conductive patch on the superior aspect of the ulceration. A second 4800 gauss magnet was placed with the North pole directed toward the skin over the electrically conductivd patch on the medial aspect of the ulceration. A third 4800 gauss magnet was placed with the South pole directed toward the skin over the electrically conductive patch on the lateral aspect of the ulceration. Each of the magnets had an appropriate hook-and-loop fastener on it to allow each attachment to the corresponding hook-and-loop fastener on the electrically conductive patch. A fourth 4800 gauss magnet was placed with the South pole directed toward the skin over the electrically conductive patch on the inferior aspect of the ulceration. After 5 weeks of treatment, the necrotic ulceration had granulated closed. The reason for the healing is thought to be increased blood circulation in the area of the ulceration.

EXAMPLE 6

A 45 year old Caucasian female presented with a diagnosis of Tarsal Tunnel Syndrome, right wrist. She was treated daily for fifteen days with doubled interferential therapy with a Dynatron 650 RS machine using magnetic electrodes. The first half of the first interferential therapy (channels 1 and 2) was given from the palmar surface of the right thumb (C6) to the palmar surface of the left fifth finger (C8). The other half of the first interferential therapy was given from the palmar surface of the left thumb (C6) to the palmar surface of the right fifth finger (C8). The first pair of leads of the second interferential therapy (channels 3 and 4) was placed on the medial palmar and lateral volar aspect of the right wrist. The second pair of leads of the second interferential therapy was placed on the lateral palmar and medial volar aspect of the right wrist. 4800 gauss magnets were placed in the wristband of a glove with the North pole directed toward the skin over each of the electrically conductive patches on the palmar aspect of the right wrist. 4800 gauss magnets were placed in the wristband of the same glove with the South pole directed toward the skin over each of the electrically conductive patch of volar aspect of the right wrist. Electrical energy was delivered for forty minutes during a treatment for a series of fifteen treatments. At the end of the second treatment, the patient was pain free. If the patient felt that the glove might make her hand too warm, an elastic band was utilized, which had a hook-and-loop fastener and 4800 gauss magnets sewn into the band, instead of the glove.

Although this invention has been disclosed and described in its preferred forms with a certain degree of particularity, it is understood that the present disclosure of the preferred forms is only by way of example and that numerous changes in the details of operation and in the combination and arrangement of parts may be resorted to without departing from the spirit and scope of the invention as hereinafter claimed.

I claim:

1. A method of treating a human comprising establishing a circuit in the human body comprising a first nerve having a first terminus adjacent an extremity of the human, a second nerve having a second terminus adjacent a different extremity of the human and a pathway between the first and second termini, the establishing step including attaching a first electrode to the extremity adjacent the first terminus of the first nerve and attaching a second electrode to the different extremity adjacent the first terminus of the second nerve; the first and second electrodes comprising an electrically conductive patch, a mechanism for applying the patch to the body and a connector for attachment to a source of electrical energy for delivering electrical energy to the patch and thereby through the circuit; and a planar magnet having a first side which is all of a north pole polarity and a second side which is all of a south pole polarity, one of the sides being juxtaposed to the patch and one of the sides facing away from the patch so a magnetic field between the poles is generally perpendicular to the patch; and delivering electrical energy substantially through the electrodes on the extremities and thereby through the circuit and applying a magnetic field perpendicular to the patch.

2. The electrode of claim 1 wherein the patch provides a length dimension and a width dimension and wherein the electrode is substantially thinner than either the length dimension or the width dimension.

3. The electrode of claim 2 wherein the patch is circular.

4. The electrode of claim 1 wherein the magnet is a permanent magnet.

5. The electrode of claim 4 wherein the magnet is at least 2400 gauss.

6. The electrode of claim 4 wherein the magnet is resilient and comprises a resin base having a magnetic material incorporated therein.

7. The electrode of claim 1 wherein the applying means comprises an adhesive layer on a first side of the patch for attachment to the body, the magnet being juxtaposed to the patch adjacent a second side.

8. The electrode of claim 7 wherein the magnet is affixed to the patch.

9. The electrode of claim 7 further comprising a hook-and-loop fastener attaching the magnet to the patch.

10. The electrode of claim 7 wherein the magnet is unattached to the patch and further comprising means for juxtaposing the magnet to the electrode.

11. The electrode of claim 1 further comprising a body encircling garment having the electrode thereon exposed to an interior of the garment for abutting the skin of a patient.

12. The electrode of claim 11 wherein the garment is a sock.

13. The electrode of claim 11 wherein the garment is a glove.

14. An electrode for delivering electrical energy to a body comprising an electrically conductive patch, means for applying the patch to the body and a connector for attachment to a source of electrical energy for delivering energy to the patch;

means receiving part of the body having at least one opening therein aligned with a desired location on the body for receiving the electrical patch; and a magnet on the receiving means having a first side which is all of a north pole polarity and a second side which is all of a south pole polarity, one of the sides being juxtaposed to the patch and one of the sides facing away from the patch so a magnetic field between the poles is generally perpendicular to the patch.

15. The electrode of claim 14 wherein the receiving means is an elastic band.

16. The electrode of claim 15 wherein the band comprises a hook-and-loop fastener affixing the magnet to the band.

17. The electrode of claim 14 wherein the receiving means comprises a sock.

18. The electrode of claim 14 wherein the receiving means comprises a glove.

19. The electrode of claim 14 further comprising a band extending over the opening, the magnet being attached to the band and overlying the opening.

20. The electrode of claim 19 wherein the band is affixed to the receiving means.

21. A method of treating a human for ailments related to the nervous system using a pair of electrodes for delivering electrical energy to a body, each electrode comprising an electrically conductive patch, means for applying the patch to the body and a connector for attachment to a source of electrical energy for delivering energy to the patch; and a planar magnet having a first side which is all of a north pole polarity and a second side which is all of a south pole polarity, one of the sides being juxtaposed to the patch and one of the sides facing away from the patch so a magnetic field between the poles is generally perpendicular to the patch; the method comprising affixing a first of the electrodes to an extremity of the human adjacent a first terminus of a first nerve on the extremity, and affixing a second of the electrodes to a different extremity of the human for establishing a circuit in the human between the first and second electrodes for delivering electrical energy through the circuit.

* * * * *